(12) United States Patent
Zhang et al.

(10) Patent No.: US 11,478,278 B2
(45) Date of Patent: Oct. 25, 2022

(54) FIXING DEVICE, INSTALLATION TOOL AND FIXING METHOD OF THE CRANIAL FLAP

(71) Applicant: CHENGDU MEDART MEDICAL SCIENTIFIC CO., LTD, Chengdu (CN)

(72) Inventors: Xiaojin Zhang, Chengdu (CN); Jun Wang, Chengdu (CN); Jian Wu, Chengdu (CN)

(73) Assignee: CHENGDU MEDART MEDICAL SCIENTIFIC CO., LTD, Chengdu (CN)

( * ) Notice: Subject to any disclaimer, the term of this patent is extended or adjusted under 35 U.S.C. 154(b) by 194 days.

(21) Appl. No.: 16/971,668

(22) PCT Filed: Aug. 29, 2019

(86) PCT No.: PCT/CN2019/103184
§ 371 (c)(1),
(2) Date: Aug. 20, 2020

(87) PCT Pub. No.: WO2021/003817
PCT Pub. Date: Jan. 14, 2021

(65) Prior Publication Data
US 2021/0228240 A1 Jul. 29, 2021

(30) Foreign Application Priority Data
Jul. 10, 2019 (CN) .......................... 201910620819.0

(51) Int. Cl.
*A61B 17/68* (2006.01)
*A61B 17/88* (2006.01)
(Continued)

(52) U.S. Cl.
CPC ............ *A61B 17/688* (2013.01); *A61B 17/92* (2013.01); *A61B 90/03* (2016.02); *A61B 2017/922* (2013.01); *A61B 2090/031* (2016.02)

(58) Field of Classification Search
CPC .. A61B 17/688; A61B 90/03; A61B 2090/031
See application file for complete search history.

(56) References Cited

U.S. PATENT DOCUMENTS

| 6,358,152 | B2 * | 3/2002 | Casutt ................. | B25B 23/1415 464/34 |
| 7,387,633 | B2 * | 6/2008 | Ahmad .................. | A61B 17/88 606/281 |

(Continued)

FOREIGN PATENT DOCUMENTS

| CN | 205697968 | 11/2016 | |
| CN | 208808621 | 5/2019 | |
| WO | WO-2015151096 A1 * | 10/2015 | ......... A61B 17/8875 |

*Primary Examiner* — Christian A Sevilla
(74) *Attorney, Agent, or Firm* — Hauptman Ham, LLP

(57) ABSTRACT

A fixing device and an installation tool and a fixing method of the cranial flap, wherein the installation tool comprises a driving part, a loading part and an over torque protection mechanism disposed between the driving part and the loading part, the driving part drives the loading part to rotate by the over torque protection mechanism, the loading part is used for tightening the cranial flap fixation device, when the torque of the driving part acting on the over torque protection mechanism is larger than the threshold value, the over torque protection mechanism will be separated from the driving part and/or the loading part. The present invention not only effectively improves the installation and disassembly efficiency of the installation tool, but also eliminates hidden safety hazards caused by uncertainties caused by human factors in the tightening process, significantly improves the safety of the installation process.

5 Claims, 3 Drawing Sheets

(51) Int. Cl.
   *A61B 90/00* (2016.01)
   *A61B 17/92* (2006.01)

(56) References Cited

U.S. PATENT DOCUMENTS

| | | | | |
|---|---|---|---|---|
| 2010/0107829 A1* | 5/2010 | Zimmerman | ....... | B25B 23/1427 173/1 |
| 2010/0251861 A1* | 10/2010 | Sixto, Jr. | ............. | B25B 23/1427 81/436 |
| 2013/0199345 A1* | 8/2013 | Nino | ...................... | A61B 90/03 81/473 |

* cited by examiner

FIXING DEVICE, INSTALLATION TOOL AND FIXING METHOD OF THE CRANIAL FLAP

RELATED APPLICATIONS

The present application is a National Phase of International Application Number PCT/CN2019/103184, filed Aug. 29, 2019, and claims the priority of China Application No. 201910620819.0, filed Jul. 10, 2019.

FIELD OF THE INVENTION

The present invention relates to the field of surgery, and more particularly to a fixing device and an installation tool and a fixing method of the cranial flap.

BACKGROUND OF THE INVENTION

The cranial flap fixation device, also known as the cranial lock, is a medical device used for fixing the cranial flap, can quickly meet the clinical fixation requirements of the cranial flap after craniotomy; it is easy to operate, fast to rotate, firm to clamp, which can effectively save operation time.

The traditional cranial flap fixation device comprises a connecting rod, and an upper disc as well as a lower disc disposed on the connecting rod; the upper disc and the connecting rod are connected by threads. When in use, rotating the upper disc to move it along the connecting rod, and finally the upper disc and the lower disc are clamped to fix the cranial flap.

In existing technology, the cranial flap fixation device is usually equipped with an installation tool; for example, the patent with publication number CN205697968U discloses a cranial flap fixation device, the cranial flap fixation device is set with a spin lock as the installation tool of the upper disc. The bottom end of the spin lock is set with a locking column, which can be inserted into the connection hole set on the upper disc, so that the spin lock can drive the upper disc to rotate to carry out the locking operation. The patent with publication number U.S. Pat. No. 7,387,633B2 also discloses a cranial flap fixation device, the bottom end of the installation tool is set with a short column that is matched with a guide hole disposed on the upper disc; when in use, the short column of the installation tool is inserted into the guide hole of the upper disc, which can enable the installation tool to drive the upper disc to rotate on the connecting rod.

Although the above mentioned installation tools can significantly simplify the tightening operation of the upper disc, the doctor cannot estimate whether the upper disc has been tightened during the operation, and the more or less force of the upper disc acting on the cranial flap will bring hidden dangers to the safety of cranial flap fixation.

BRIEF SUMMARY OF THE INVENTION

The present invention aims to provide a fixation device and an installation tool and a fixing method of the cranial flap, to solve the problem caused by the doctor's inability to intuitively estimate whether the upper disc has been tightened during the operation.

The present invention is realized by the following technical scheme:

A installation tool of the cranial flap fixation device, comprising a driving part, a loading part and an over torque protection mechanism disposed between the driving part and the loading part; the driving part drives the loading part to rotate by the over torque protection mechanism, the loading part is used for tightening the cranial flap fixation device; when the torque of the driving part acting on the over torque protection mechanism is more than the threshold value, the over torque protection mechanism is separated from the driving part and/or the loading part.

In existing technology, the cranial flap fixation device is usually equipped with the installation tool. Although the all-in-on installation tool can significantly simplify the tightening operation of the upper disc, the doctor cannot estimate whether the upper disc is tightened during the operation. When the torque applied on the installation tool is too large, it will significantly increase the clamping force of the upper disc on the cranial flap, which may cause difficulty in disassembly of the upper disc, or cause indentation or damage to the cranial flap; when the torque applied on the installation tool is too small, the clamping force of the upper disc is not enough to fix the cranial flap stably, which creates a safety risk for the subsequent surgical operations. It can be seen that larger or smaller of the torque applied on the installation tool will bring hidden dangers to the safety of cranial flap fixation. At present, the doctor mainly relies on experience to estimate whether the upper disc is tightened when tightening the cranial flap fixation device. The purpose is to avoid that the torque is too small to ensure the stability of the clamping, so the torque applied on the installation tool is usually larger, and it will wear the cranial surface inevitably, or cause difficulties in the subsequent removal of the upper disc, which reduces the effectiveness and efficiency of surgery. However, high-intensity craniotomy often requires rapid tightening of at least three cranial flap fixation devices, so the doctor needs to estimate the torque of multiple cranial flap fixation devices in a short time, which will inevitably cause differences in the torque applied to the multiple cranial flap fixation devices. The different clamping forces exerted by multiple upper discs result in uneven force on the cranial flap, which is prone to produce internal stress and cause damage to the cranial flap.

In order to solve the above problems, the inventor improves the structure of the existing installation tool by setting the installation tool to a two-section structure, and setting an over torque protection mechanism in the installation tool. According to the set torque threshold value, when the torque applied on the installation tool exceeds the threshold value, the installation tool cannot provide torque to the upper disc, the clamping force of the upper disc acting on the cranial flap will reach the upper limit.

Specifically, identical to the prior art, the installation tool of the cranial flap fixation device includes a through hole penetrating through the upper end surface and lower end surface thereof, and the installation tool is shuttled on the connecting rod of the cranial flap fixation device through the through-hole, so that the installation tool can move along the connecting rod. At least one locking column is also set on the lower end surface of the installation tool, and the locking column matches the fastening hole set on the upper disc, so that the locking column can cooperate with the fastening hole, and then drive the upper disc to rotate along the connecting rod.

Different from the prior art, the cranial flap fixation device includes a driving part, a loading part, and an over torque protection mechanism designed between the driving part and the loading part, wherein, the driving part is used to drive the loading part to rotate by the over torque protection mechanism, the over torque protection mechanism acts as a force transmission mechanism to transfer the torque applied on the driving part to the loading part, and the loading part is used for tightening the cranial flap fixation device. Preferably, the driving part and the loading part are coaxially fitting.

When the torque of the driving part acting on the over torque protection mechanism is less than or equal to the threshold value, the driving part drives the loading part to rotate synchronously by the over torque protection mechanism, the installation tool is in the driving state, and the torque applied on the driving part can be transferred to the loading part through the over torque protection mechanism. When the torque of the driving part acting on the over torque protection mechanism is larger than the threshold value, the over torque protection mechanism is separated from the driving part and/or the loading part, the installation tool is in the failure state, and the torque applied on the driving part cannot be transferred to the loading part through the over torque protection mechanism.

The installation tool works as follows: when the clamping force of the upper disc on the cranial flap reaches the upper limit, continuing to rotate the driving part will cause the torque to exceed the upper limit value, and the installation tool will switch from the driving state to the failure state; on one hand, the clamping force of the upper disc on the cranial flap cannot be increased, and on the other hand, the counterforce of the driving part acting on the doctor's hand drops sharply, and the driving part is slipping, which can intuitively and quickly remind the doctor that the torque has reached the threshold value.

The threshold value of the above-mentioned over torque protection mechanism corresponds to the upper limit value of the clamping force of the upper disc on the cranial flap. The range of the threshold value can be determined by the connection strength of the over torque protection mechanism with the driving part and the loading part, by the strength, hardness and size position of the over torque protection mechanism itself, and also can depend on the material, the arm of force, size of the thin column, processing technology and other influencing factors. For this reason, over torque protection mechanisms with different threshold values can be provided for different cranial flaps, allowing the doctor to know the magnitude of the clamping force applied on the cranial flap before fixation. For example, for a cranial flap with low hardness, the threshold value of the over torque protection mechanism can enable the upper disc to provide a clamping force of less than or equal to 40 N to the cranial flap. Corresponding to the cranial flap with high hardness, in order to avoid difficulty in disassembly, a clamping force of 20-50 N is provided.

Through the above structure, during the installation of the cranial flap fixation device, the doctor does not need to estimate the torque, and only applying a torque that exceeds the threshold value can provide precise clamping force on the multiple cranial flap fixation devices in a short time, so that the clamping forces applied on the cranial flap by the upper discs are consistent, which not only effectively improves the installation and disassembly efficiency of the installation tool, but also eliminates the safety hazards caused by the uncertainty caused by human factors during the tightening process, significantly improves the safety of the installation process and effectively protects the cranial flap; in addition, by setting different threshold values, the installation mechanism can be applied to cranial flaps with different hardness, the doctor can select the installation tool with appropriate threshold value before surgery, which further improves the stability of the clamping.

As a preferred embodiment of the present invention, the installation tool can continuously switch between the driving state and the failure state. The installation tool includes a first baffle fixed on the driving part and a second baffle fixed on the loading part, wherein, the first baffle or the second baffle serves as the over torque protection mechanism. When in use, rotating the driving part makes the first baffle contact the second baffle, and continuing to rotate the driving part to make the first baffle provide torque to the second baffle and drive the second baffle to rotate, and then the installation tool will enter the driving state. When the clamping force of the upper disc on the cranial flap reaches the upper limit value, the torque provided by the driving state cannot further rotate the loading part, increasing the torque will cause the torque to exceed the threshold value and the first baffle to disconnect from the second baffle; the first baffle continues to rotate but the second baffle remains stationary, the installation tool remains in a failure state, and the over torque protection mechanism is separated from the driving part or the loading part. After the driving part rotates one turn, the first baffle will contact the second baffle again, form a connection and drive the loading part to rotate by the second baffle, and the installation tool enters the driving state again. By analogy, the installation tool can continuously switch between the driving state and the failure state to ensure that the torque does not exceed the upper limit value. Preferably, in driving state, the lower part of the first baffle is in contact with the upper part of the second baffle. Preferably, both the lower part of the first baffle and the upper part of the second baffle are disposed with an anti-wear layer that can not only reduce the wear of the first baffle and the second baffle, but also produce a certain deformation, which is beneficial to the separation of the first baffle and the second baffle, thus extending the service life of the first baffle and the second baffle. In this structure, the connection strength of the first baffle and the second baffle determines the torque threshold value. In this technical scheme, the installation tool can be used repeatedly, but each time when it enters the driving state from the failure state, a certain torque will be generated, which makes the upper disc produce the impact to the cranial flap fragment.

As another preferred embodiment of the present invention, the installation tool can only switch from the driving state to the failure state for a limited number of times. Specifically, when the torque of the driving part acting on the over torque protection mechanism is larger than the threshold value set by the over torque protection mechanism, the over torque protection mechanism is simultaneously separated from the driving part and the loading part. In this technical scheme, the installation tool includes a third baffle fixed on the driving part and a fourth baffle fixed on the loading part, wherein the third baffle or the fourth baffle serves as the over torque protection mechanism. When in use, rotating the driving part makes the third baffle contact the fourth baffle, and continuing to rotate the driving part makes the third baffle provide torque to the fourth baffle and drive the fourth baffle to rotate, and the installation tool enters the driving state. When the clamping force of the upper disc on the cranial flap reaches the upper limit value, the torque provided by the driving state cannot further rotate the loading part, increasing the torque will cause the torque to exceed the threshold value and the third baffle to disconnect from the driving part and/or the fourth baffle to disconnect from the loading part, or the third baffle to break and/or the fourth baffle to break, then the installation tool will enter the failure state, and the over torque protection mechanism will be simultaneously separated from the driving part and the loading part. In this structure, the connection strength of the third baffle and the driving part, lower limit values of the connection strength of the fourth baffle and the loading part, the hardness of the third baffle and the hardness of the fourth baffle determine the torque threshold value. In this technical scheme, the installation tool has a limited number of switching from the driving state to the failure state, when all the over torque protection mechanisms fail, the installation tool will no longer be able to switch from the failure state to the driving state. Although the structure cannot be reused, but after it enters the failure state for the last time, it will no longer generate torque on the upper disc, which avoids the impact of the upper disc on the cranial flap fragment.

In some embodiments, a groove with an upward opening is disposed on the driving part, the depth of the groove depends on the overall structural strength of the driving part, the groove is beneficial to reduce the weight of the driving part, thereby reducing the total weight of the installation tool.

In some embodiments, all components of the installation tool can be made of medical degradable or non-degradable materials such as PLA, PP, PC, PS, ABS, and preferably made of PLA. The use of the same degradable material not only ensures the safety of the installation tool, reduces the total weight of the installation tool, but also broadens the doctor's field of vision with the transparent driving part and the loading part, which is beneficial to the craniotomy.

Further, a closed accommodating cavity is formed between the driving part and the loading part, and the over torque protection mechanism is disposed in the accommodating cavity. In the driving state or failure state, the accommodating cavity is always in a closed state, so that the anti-wear layer and the baffle are always located in the closed accommodating cavity after falling off, which prevents the above parts from falling into the risk area and affecting intracranial surgery.

As a preferred embodiment of the over torque protection mechanism of the present invention, the over torque protection mechanism comprises a thin column, the thin column is fixed on the bottom surface of the driving part; the loading part includes a groove with an upward opening, the groove and the bottom surface of the driving part form the closed accommodating cavity, and a baffle is disposed in the groove; the loading part is driven to rotate through the cooperation of the thin column and the baffle. When the torque of the driving part acting on the thin column is larger than the threshold value, the thin column will be broken and/or the thin column will fall off from the bottom surface of the driving part. In this technical scheme, the groove of the loading part and the bottom surface of the driving part form the closed accommodating cavity, and the baffle fixed on the groove and the thin column fixed on the bottom surface of the driving part are disposed in the accommodating cavity, wherein the thin column is used as the over torque protection mechanism to cooperate with the baffle and drive the baffle to rotate. When the clamping force of the upper disc on the cranial flap reaches the upper limit, the loading part stops rotating, and after receiving a greater torque, the torque of the driving part acting on the thin column will be greater than the threshold value, the thin column will be broken and/or fall off from the bottom surface of the driving part, causing the thin column to separate from the driving part and the loading part at the same time, and slipping phenomenon occurs in the driving part to ensure that the upper disc will not be over-tightened after being firmly fixed. In this technical scheme, the threshold value of torque is related to the connection strength of the thin column and the driving part and/or the strength and hardness of the thin column, preferably, the threshold value of the torque is mainly related to the hardness and strength of the thin column.

Further, several baffles are disposed in the groove, and the baffles divide the closed accommodating cavity into many chambers, and each one of the chambers is disposed with the thin column. In this technical scheme, baffles and thin columns are disposed in the containing cavity. The baffles and thin columns divide the closed accommodating cavity into the multiple chambers, and the chambers can be closed chambers or unclosed chambers. At least one thin column is disposed in each chamber, and preferably, only one thin column is disposed in each chamber. The size of the chambers can be the same or different, the size of the chamber determines the moving distance of the thin column in the chamber, which in turn affects the rotation angle of the driving part.

In some embodiments, the groove is disposed with a first chamber and a second chamber, wherein the first chamber is disposed with a first thin column, and the second chamber is disposed with a second thin column. In the initial state, the distance from the first thin column to the baffle of the first chamber is equal to the distance from the second thin column to the baffle of the second chamber, meanwhile, the hardness of the first thin column is equal to the hardness of the second thin column. Through the above settings, the installation tool can only switch from the driving state to the failure state once, the tightening efficiency is higher, at the same time, after some thin columns are broken due to the misoperation, the above mechanism avoids the situation that the installation tool directly enters the failure state. The technicians in this field should understand that more than two chambers and more than two thin columns can be set according to the above settings to further improve the fault tolerance rate.

In some embodiments, the distance from the first thin column to the baffle of the first chamber is smaller than the distance from the second thin column to the baffle of the second chamber, meanwhile, the hardness of the first thin column is less than the hardness of the second thin column. Through the above settings, in the process of tightening the cranial flap fixation device, the installation tool can switch from the driving state to the failure state twice, in which there is a time difference between the first switch and the second switch, and the torque required for the second switch is larger than that required for the first switch, so as to achieve a wider range of the threshold value. When in use, the clamping force of the upper disc on the cranial flap after the first switch is not enough to hold the cranial flap firmly, the doctor can further increase the torque until the second threshold value is reached, thereby providing a more stable clamping force on the cranial flap, reducing the safety risks. The technicians in this field should understand that more than two chambers and more than two thin columns can be set according to the above settings to achieve at least two or more threshold values and further improve the universality and accuracy of the installation tool.

In some embodiments, one baffle can correspond to multiple thin columns, and one thin column can also correspond to multiple baffles.

The driving part and the loading part can be connected in various ways. In some embodiments, a stuck slot is disposed on the bottom of the driving part, and a stuck convex matching the stuck slot is disposed on the bottom of the loading part, so that the loading part cannot be separated from the driving part along the direction of the central axis, but can rotate around the central axis.

As a preferred connection method of the driving part and the loading part in the present invention, a guide tube is disposed on the bottom surface of the driving part, the guide tube connects the lower end face of the loading part and the upper end face of the driving part, a convex plate located below the loading part is disposed on the guide tube, and the side wall of the guide tube is also opened with an incision. The guide tube penetrates the whole installation tool, and the inner diameter of the guide tube matches the outer diameter or the thread outer diameter of the connecting rod of the cranial flap fixation device, allowing the installation tool to move along the connecting rod up and down. The bottom end of the guide tube penetrates the loading part, and the outer wall of the guide tube is disposed with the boss. When the driving part and the loading part are assembled, the boss is located below the loading part. Preferably, the distance between the upper surface of the boss and the bottom surface of the driving part is equal to the height of the loading part, making the accommodating cavity between the groove inside the loading part and the bottom surface of the driving part to be always closed in the driving state or the failure state. The side wall of the guide tube is also opened with the incision, preferably, the incision is an inverted triangle. When installing the driving part and the stuck part, first align the hole on the loading part with the guide tube of the driving part, set the loading part on the guide tube, push the loading part until the hole contacts the boss, rotate the load part to align the thin column and the chamber, and forcefully push the loading part toward the direction of the driving part, then the guide tube will have a certain deformation due to the existence of the incision, which makes the outer diameter of the boss decrease; after the hole of the loading part passes through the boss smoothly, the outer diameter of the boss recovers and forms a stuck connection at the bottom of the loading part. The above connection method realizes that the accommodating cavity between the groove inside the loading part and the bottom surface of the driving part is always closed in the driving state or the failure state; at the same time, the guide tube used as the stuck part, simplifies the overall structure of the installation tool, reduces the use of components, and reduces the total mass of the installation tool; not only that, the loading part and the driving part are always connected together, which makes the integrity of the installation tool stronger, facilitates the storage, disassembly and use of the installation tool.

Further, the loading part comprises an installation table, the installation table is disposed on the bottom surface of the loading part, the installation table is set with a locking column. The installation table can further improve the stability of the locking column and avoid the locking column from breaking during the tightening process. Preferably, the installation platform has a hollow structure to reduce the total mass of the installation tool.

Further, a first anti-slip part is set on the driving part, and a second anti-slip part is set on the loading part. The first anti-slip part can effectively increase the friction on the surface of the driving part, and facilitate to apply torque to the driving part. Preferably, the first anti-slip part is an anti-slip rib, which can not only increase the friction on the surface of the driving part, but also increase the structural strength of the driving part. When the installation tool fails due to misoperation, as an emergency measure, the doctor can directly apply torque on the loading part through the second anti-slip part, meanwhile, the second anti-slip part facilitates the disassembly of the cranial flap fixation device. Preferably, the second anti-slip part is an anti-slip rib. In addition to the anti-slip rib, the first anti-slip part or the second anti-slip part can also use rubber, bump and other existing technical means to increase the friction on the surface of the driving part and the loading part.

The present invention also provides a cranial flap fixation device, comprising a connecting rod, an upper disc and a lower disc disposed on the connecting rod, wherein the upper disc and the connecting rod are connected by threads, and a fastening hole is set on the upper disc. The connection between the upper disc and the connecting rod is threaded connection, which can enable the upper disc to gradually increase the clamping force on the cranial flap; the lower disc can either be fixed at the bottom of the connecting rod or connected with the connecting rod by threads; preferably, there is a certain working gap between the lower disc and the connecting rod, which enables the lower disc to tilt at a certain angle relative to the horizontal plane, allowing to adaptively adjust its angle during installation to better fit the cranial flap. The cranial flap fixation device further comprises any of the above mentioned installation tool; the locking column is disposed on the bottom end of the installation tool and the size of the locking column matches the size of the fastening hole, which enables the locking column to insert into the fastening hole, and then the upper disc is driven to rotate along the connecting rod through the installation tool.

In some embodiments, a first tooth is installed on the bottom surface of the upper disc; the first tooth is a forward and backward stop tooth and ensures that the upper disc can maintain sufficient frightening force after the installation tool is tightened.

In some embodiments, a second tooth is installed on the top surface of the lower disc; the second tooth is a fixed tooth, the fixed tooth can further improve the stability of the cranial flap.

Further, a handle is disposed on the top of the connecting rod and a handle stuck slot is disposed on the top of the driving part; the handle can be matched with the handle stuck slot. The handle not only facilitates the doctor to hold the connecting rod, but also prevents the installation tool from detaching from the connecting rod, ensuring that the installation tool is always sleeved on the connecting rod during craniotomy. The handle stuck slot is disposed on the top of the driving part, the handle can be matched with the handle stuck slot; during craniotomy, the doctor can lift the installation tool along the connecting rod and fix it on the handle if necessary to broaden the surgical field of vision, and observe the intracranial situation in a better way.

Compared with the prior art, the present invention has the following advantages and beneficial effects:

1. During the installation of the cranial flap fixation device, the doctor does not need to estimate the torque, and only applies a torque that exceeds the threshold value to apply precise clamping force on the multiple cranial flap fixation devices in a short time, so that the clamping force applied on the cranial flap by the upper discs are consistent, which not only effectively improves the installation and disassembly efficiency of the installation tool, but also eliminates safety hazards caused by uncertainties caused by human factors during the tightening process, significantly improves safety of the installation process, and effectively protects the cranial flap; in addition, by setting different threshold values, the installation mechanism can be applied to cranial flaps with different hardness, the doctor can select the installation tool with appropriate threshold value before craniotomy, which further improves the stability of the clamping;

2. The installation tool provided by the present invention can continuously switch between the driving state and the failure state, and can also only switch from the driving state to the failure state for a limited number of times; the former can be used repeatedly, and after the latter enters the failure state for the last time, it will no longer generate torque on the upper disc, which avoids the impact of the upper disc on the cranial bone fragment;

3. In the present invention, a closed accommodating cavity is formed between the driving part and the loading part to accommodate the over torque protection mechanism; when in driving state or failure state, the accommodating cavity is always in a closed state, so that the anti-wear layer and the baffle are always located in the closed accommodating cavity after falling off, which prevents the component from falling into the risk area and affecting intracranial surgery;

4. During the process of tightening the cranial flap fixation device in the present invention, the installation tool can switch from driving state to failure state twice, in which there is a time difference between the first switch and the second switch, and the torque required for the second switch is larger than that required for the first switch, so as to achieve a wider range of the threshold value. In use, when the clamping force of the upper disc on the cranial flap after the first switch is not enough to fix the cranial flap firmly, the doctor can further increase the torque until the second threshold value is reached, thereby providing a more stable clamping force on the cranial flap, and reducing safety risks;

5. The present invention optimizes the connection mode of the driving part and the loading part, and realizes that the accommodating cavity between the groove inside the loading part and the bottom surface of the driving part is always closed in the driving state or the failure state; at the same time, the guide tube is used as the stuck part, which simplifies the overall structure of the installation tool, reduces the use of components, and reduces the total mass of the installation tool; besides that, the loading part and the driving part are always connected together, which makes the integrity of the installation tool stronger and facilitates the storage, disassembly and use of the installation tool;

6. The present invention provides a cranial flap fixation device equipped with any of the above mentioned installation tools, which eliminates safety hazards caused by uncertainties caused by human factors during the tightening process, and significantly improves the safety of the installation process.

BRIEF DESCRIPTION OF THE DRAWINGS

The drawings described here are used to provide a further understanding of the embodiments of the present invention, which forms a part of the application rather than a limitation to the embodiments of the present invention. In the attached picture.

DETAILED DESCRIPTION OF THE PREFERRED EMBODIMENTS

Figure 1:
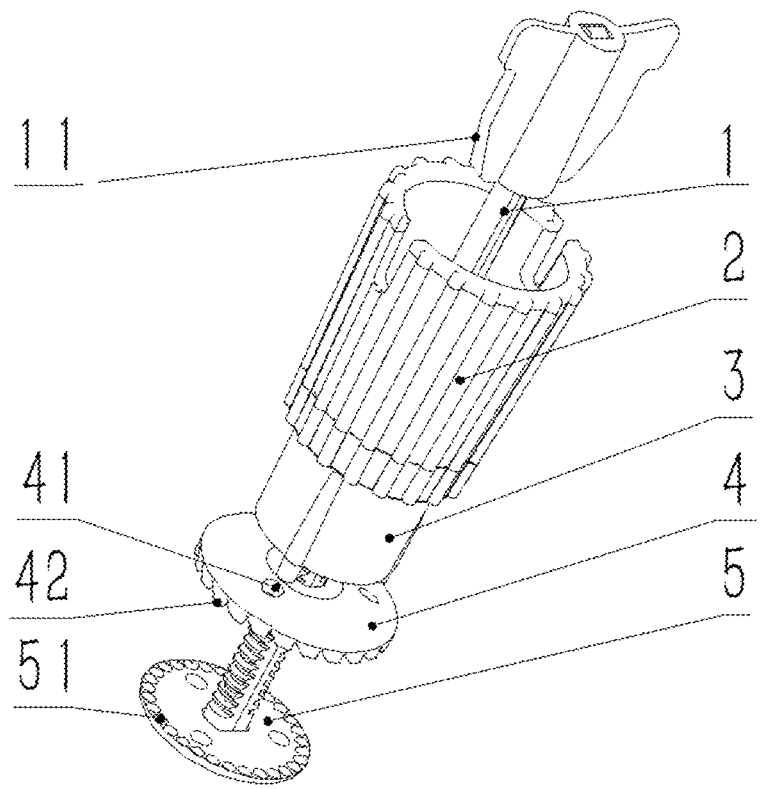
FIG. 1 is a schematic structural diagram of the cranial flap fixation device in embodiment 1 of the present invention.

In order to make the objectives, technical solutions, and advantages of the present invention clearer, the following describes the present invention in further detail with reference to the embodiments and drawings; the exemplary embodiments of the present invention and the description thereof are only used to explain the present invention, not as a limitation of the present invention.

In the description of the present invention, it should be understood that the terms "front", "rear", "left", "right", "upper", "lower", "vertical", "horizontal", "high", "low", "inner", "outer" indicating the orientation or the positional relationship are based on the orientation or positional relationship shown in the drawings, and are only for the convenience of describing the present invention and simplifying the description, rather than indicating or implying that the device or the element must have a specific orientation, be constructed and operated in a specific orientation, and therefore cannot be understood as a limitation to the protection scope of the present invention.

Embodiment 1

Figure 2:
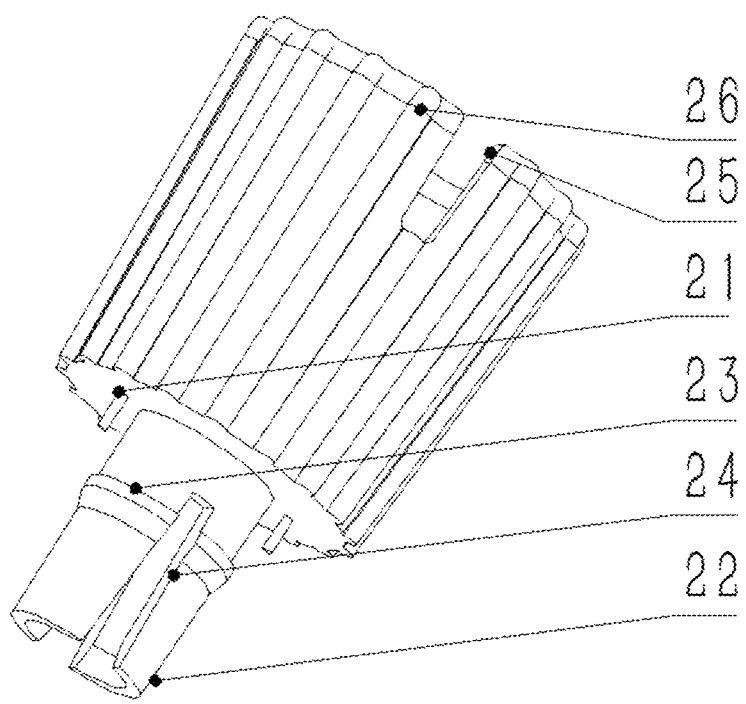
FIG. 2 is a schematic structural diagram of the upper section of the installation tool in embodiment 1 of the present invention.
Figure 3:
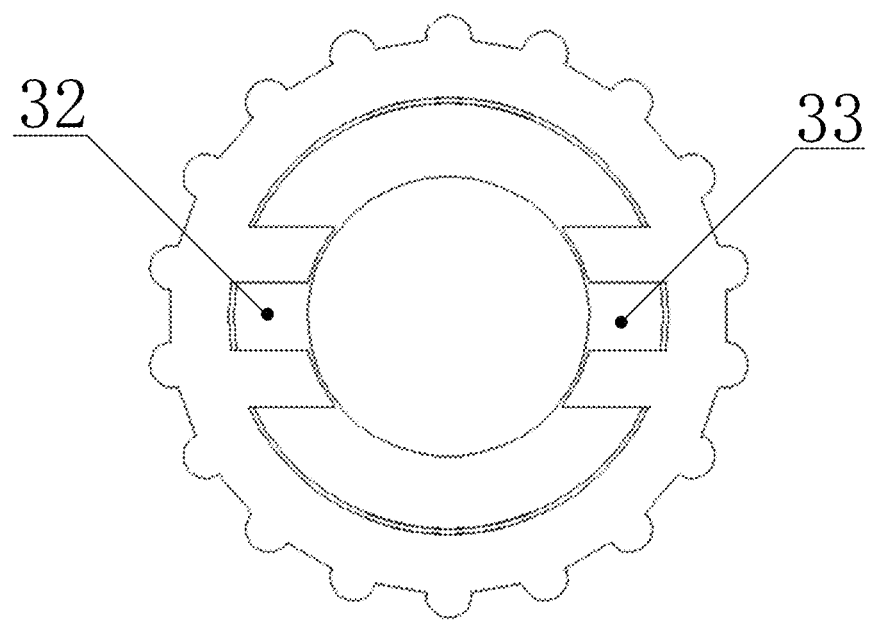
FIG. 3 is a planform of the low section of the installation tool in embodiment 1 of the present invention.

The cranial flap fixation device shown in FIGS. 1 to 3, comprises a connecting rod 1, an upper disc 4 and a lower disc 5 disposed on the connecting rod 1, wherein the upper disc 4 and the connecting rod 1 are connected by threads, a fastening hole 41 is set on the upper disc 4.

The cranial flap fixation device further comprises an installation tool sleeved on the connecting rod 1, wherein a locking column 35 is disposed on the bottom end of the installation tool, and the size of the locking column 35) matches the size of the fastening hole 41; the over torque protection mechanism comprises a thin column 21 fixed on the bottom surface of the driving part 2; the loading part 3 includes a groove with an upward opening, the groove and the bottom surface of the driving part 2 form the closed accommodating cavity, and a plurality of baffles 31 are disposed in the groove, the plurality of baffles 31 form a first chamber 32 and a second chamber 33 in the groove, the size of the first chamber 32 and the second chamber 33 are the same, the two thin columns 21 are respectively located in the first chamber 32 and the second chamber 33.

As shown in FIG. 3, in the initial state, the distance from the thin column 21 in the first chamber 32 to the baffle 31 of the first chamber 32 is equal to the distance from the thin column 21 in the second chamber 33 to the baffle 31 of the second chamber 33, meanwhile, the hardness of the thin column in the first chamber 32 is equal to the hardness of the thin column in the second chamber 33. The loading part 3 is driven to rotate through the cooperation of the thin column 21 and the baffle 31; when the torque of the driving part 2 acting on the thin column 21 is larger than the threshold value, the thin column 21 is broken and/or the thin column 21 falls off from the bottom surface of the driving part 2.

A guide tube 22 is disposed on the bottom surface of the driving part 2, the guide tube connects the lower end face of the loading part 3 and the upper end face of the driving part 2, a boss 23 located below the loading part 3 is disposed on the outer wall of the guide tube 22, and the side wall of the guide tube 22 is also opened with an incision 24.

Through the above structure, when in use, the doctor does not need to estimate the torque, and only applies a torque that exceeds the threshold value to apply precise clamping force on the multiple cranial flap fixation devices in a short time, so that the clamping forces applied on the cranial flap by the upper discs are consistent, which not only effectively improves the installation and disassembly efficiency of the installation tool, but also eliminates safety hazards caused by uncertainties caused by human factors during the tightening process, significantly improves the safety of the installation process, and effectively protects the cranial flap; in addition, by setting different threshold values, the installation mechanism can be applied to cranial flaps with different hardness, the doctor can select the installation tool with appropriate threshold value before craniotomy, which further improves the stability of the clamping.

In the above structure, the installation tool can only switch from driving state to failure state once, and the tightening efficiency is higher. At the same time, after some thin columns are broken due to misoperation, the above mechanism avoids the situation that the installation tool directly enters the failure state.

In some embodiments, a first tooth is installed on the bottom surface of the upper disc to ensure that the upper disc can maintain sufficient pre-tightening force after the installation tool is tightened; a second tooth installed on the top surface of the lower disc can further improve the stability of the cranial flap.

In some embodiments, the number of the baffle 31 can be one, and the number of the thin column 21 can be one to simplify the structure of the installation tool.

In some embodiments, the installation tool includes at least two chambers and at least thin columns 21, the thin columns 21 are in one-to-one correspondence with the chambers, the distance between each thin column 21 to the baffle 31 of the corresponding cavity are the same, and the hardness of each thin column 21 is the same.

In this technical scheme, the connection mode of the driving part and the loading part realizes that the accommodating cavity between the groove inside the loading part and the bottom surface of the driving part is always closed in the driving state or the failure state; at the same time, the guide tube is used as the stuck part, which simplifies the overall structure of the installation tool, reduces the use of components, and reduces the total mass of the installation tool; besides that, the loading part and the driving part are always connected together, which makes the integrity of the installation tool stronger, facilitates the storage, disassembly and use of the installation tool.

Embodiment 2

Figure 4:
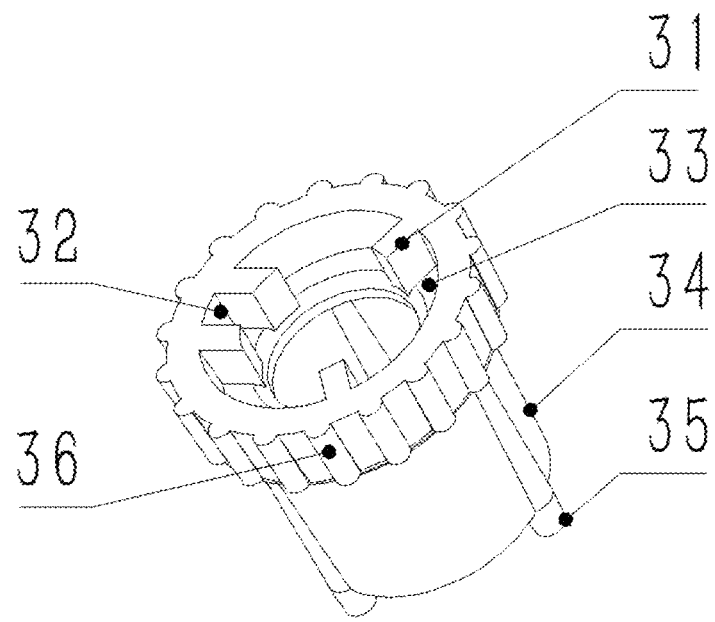
FIG. 4 is a schematic structural diagram of the low section of the installation tool in embodiment 2 of the present invention.

As shown in FIG. 4, based on the embodiment 1, the size of the first chamber 32 is smaller than the size of the second chamber 33. When the driving part 2 is combined with the loading part 3, in the initial state, the distance from the thin column 21 in the first chamber 32 to the baffle 31 of the first chamber 32 is smaller than the distance from the thin column 21 in the second chamber 33 to the baffle 31 of the second chamber 33; meanwhile, the hardness of the thin column in the first chamber 32 is smaller than that of the thin column in the second chamber 33.

With the above settings, in the process of tightening the cranial flap fixation device, the installation tool can switch from driving state to failure state twice, in which there is a time difference between the first switch and the second switch, and the torque required for the second switch is greater than that required for the first switch, so as to achieve a wider range of the threshold value. In use, when the clamping force of the upper disc on the cranial flap after the first switch is not enough to fix the cranial flap firmly, the doctor can further increase the torque until the second threshold value is reached, thereby providing a more stable clamping force on the cranial flap, and reducing the safety risks.

In some embodiments, the arc of the second chamber 33 is 2 to 4 times as large as the arc of the first chamber 32.

In some embodiments, the groove with an upward opening is disposed on the driving part, the depth of the groove depends on the overall structural strength of the driving part, the groove is beneficial to reduce the weight of the driving part and thus reduce the total weight of the installation tool.

In some embodiments, all components of the installation tool can be made of PLA.

Embodiment 3

Figure 5:
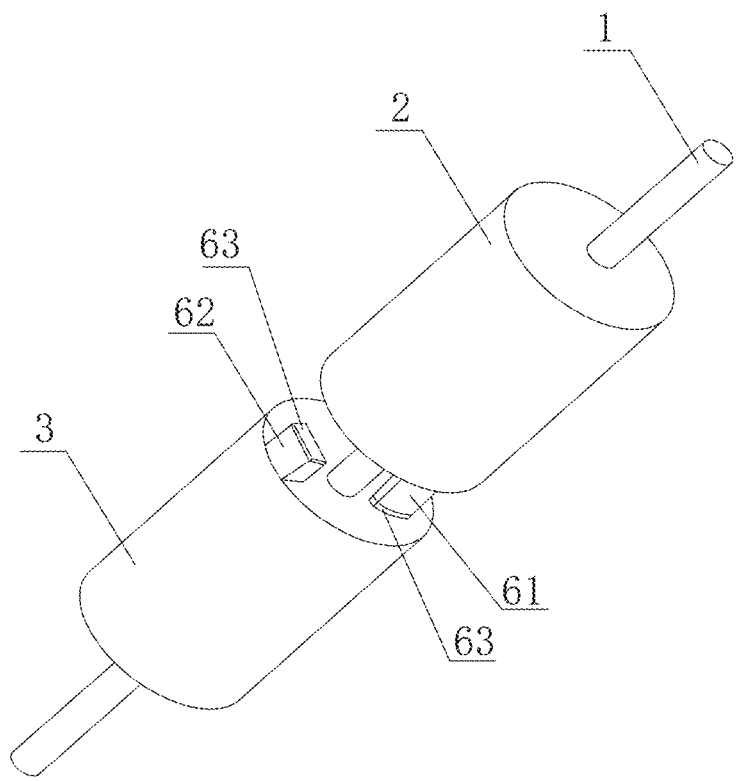
FIG. 5 is a schematic structural diagram of the installation tool in embodiment 3 of the present invention.

As shown in FIG. 5, an alternative technical scheme of the over torque protection mechanism is provided by the basis of the above-mentioned embodiment. In this technical scheme, the installation tool can continuously switch between driving state and failure state.

Specifically, the installation tool includes a first baffle 61 fixed on the driving part 2 and a second baffle 62 fixed on the loading part 3, wherein the first baffle 61 or the second baffle 62 serves as an over torque protection mechanism.

When in use, rotate the driving part to make the first baffle 61 contact the second baffle 62, continue to rotate the driving part 2 to make the first baffle 61 provide torque to the second baffle 62 and drive the second baffle 62 to rotate until the installation tool enters driving state.

When the clamping force of the upper disc 4 on the cranial flap reaches the upper limit value, the torque provided by the driving state cannot further rotate the loading part, increasing the torque will cause the torque to exceed the threshold value, which causes the first baffle 61 to disconnect from the second baffle 62, the first baffle 61 continues to rotate but the second baffle 62 remains stationary, the installation tool enters the failure state, and the over torque protection mechanism is separated from the driving part or the loading part.

After the driving part rotates one turn, the first baffle 61 will contact the second baffle 62 again and form a connection, and drive the loading part 3 to rotate by the second baffle 62, and then the installation tool enters the driving state again. By analogy, the installation tool can continuously switch between driving state and failure state to ensure that the torque does not exceed the upper limit value.

In some embodiments, both the lower part of the first baffle 61 and the upper part of the second baffle 62 are disposed with an anti-wear layer 63; the anti-wear layer can not only reduce the wear of the first baffle and the second baffle, but also produce a certain deformation, which is beneficial to the separation of the first baffle and the second baffle, thereby extending the service life of the first baffle and the second baffle.

In this structure, the connection strength of the first baffle 61 and the second baffle 62 determines the torque threshold value. The installation tool can be used repeatedly, but each time when it enters the driving state from the failure state, a certain torque will be generated, which makes the upper disc produce the impact to the cranial bone fragment.

Embodiment 4

Figure 6:
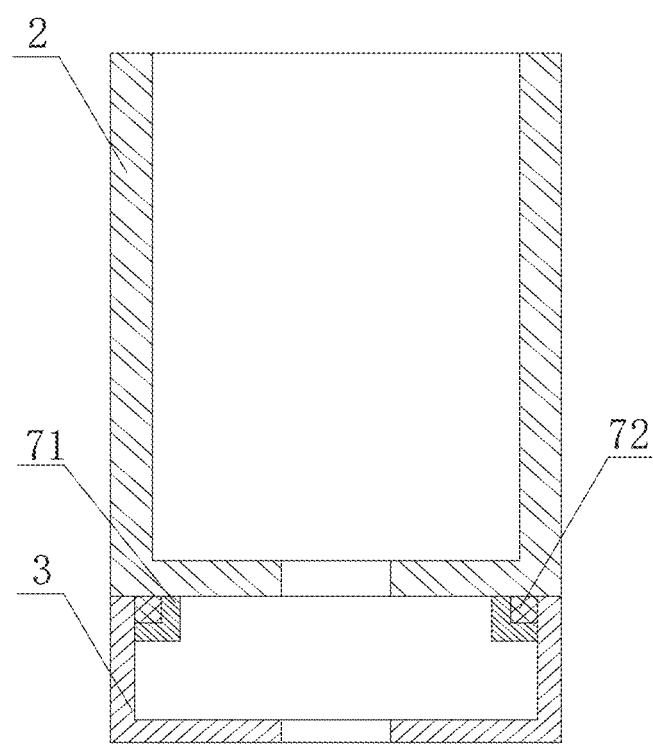
FIG. 6 is a schematic diagram of the connection relationship between the driving part and the loading part in the embodiment 4 of the present invention.

As shown in FIG. 6, an alternative technical scheme for the connection structure of the driving part 2 and the loading part 3 is provided by the basis of the above-mentioned embodiment.

The stuck slot 71 is disposed on the bottom of the driving part 2, and a stuck convex 72 matching the stuck slot 71 is disposed on the bottom of the loading part 3, so that the loading part cannot be separated from the driving part along the direction of the central axis, but can rotate around the central axis.

Embodiment 5

As shown in FIGS. 1 to 3, the handle 11 is disposed on the top of the connecting rod 1, the handle stuck slot 25 is disposed on the top of the driving part 2, and the handle 11 can be matched with the handle stuck slot 25; the loading part 3 further comprises the installation table 34, the installation table 34 is disposed on the bottom surface of the loading part 3, the installation table 34 is set with the locking column 35; the first anti-slip part 26 is set on the driving part, and a second anti-slip part 36 is set on the loading part.

Embodiment 6

The using method of the cranial flap fixation device includes the following steps:
(A) preparation work, assembling the installation tool, and setting the installation tool on the corresponding cranial flap fixation device;
(B) placing the cranial flap fixation device around the cranial flap to be fixed;
(C) cranial flap restoration, gently lifting the handle with the left hand to make the lower disc of the cranial flap fixation device close to the inner surface of the skull; aligning the locking column of the installation tool with the fastening hole of the upper disc, and turning the installation tool clockwise with right hand until the installation tool slips in the failure state, to confirm that the upper disc is in contact with the cranial surface and fixed firmly;
(D) repeating the steps (B)-(C) to install other cranial flap fixation devices until all the cranial flap fixation devices are evenly fixed around the cranial flap.

In the above operation, step (A) specifically includes the following steps:
(A1) aligning the hole on the loading part 3 with the guide tube 22 of the driving part 2, and then setting the loading part 3 on the guide tube 22;
(A2) pushing the loading part 3 until the hole contacts the boss 23, and then rotating the loading part 3 to put the thin column 21 into the corresponding chamber;
(A3) pushing the loading part 3 in the direction of the driving part 2, the guide tube 22 has a certain deformation due to the existence of the incision 24, which makes the outer diameter of the boss 23 decrease;
(A4) after the hole of the loading part 3 passes through the boss 23, the outer diameter of the boss 23 recovers and forms a stuck connection at the bottom of the loading part 3.

Through the above method, when the doctor installs the cranial flap fixation device, the doctor only needs to provide the driving part 2 with the torque larger than the threshold value, so that after the cranial flap is tighten by the upper disc 4, the installation tool will switch from the driving state to the failure state; on one hand, the clamping force of the upper disc on the cranial flap cannot be increased; on the other hand, the reaction force of the driving part acting on the doctor's hand drops sharply, and the driving part is slipping, which can intuitively and quickly remind the doctor that the torque has reached the threshold value.

The "first", "second" (for example, the first anti-skip part, the second anti-skip part, the first chamber, the first chamber) used herein are only used to distinguish the corresponding components for clarity of description. It is not intended to limit any order or emphasize importance. In addition, the term "connected" used in this text may be directly connected or indirectly connected via other components unless otherwise specified.

The specific embodiments described above describe the purpose, technical solutions and beneficial effects of the present invention in further detail. It should be understood that the above are only specific embodiments of the present invention and are not intended to limit the protection scope of the present invention, any modification, equivalent replacement, improvement made within the spirit and principle of the present invention shall be included in the protection scope of the present invention.

What is claimed is:

1. An installation tool for installing a cranial flap fixation device, comprising a driving part, a loading part and an over torque protection mechanism disposed between the driving part and the loading part; wherein the driving part drives the loading part to rotate by the over torque protection mechanism and the loading part is used for tightening the cranial flap fixation device; wherein when a torque of the driving part acting on the over torque protection mechanism is larger than a threshold value, the over torque protection mechanism will be separated from the driving part and/or the loading part; wherein a closed accommodating cavity is formed between the driving part and the loading part, and the over torque protection mechanism is disposed in the accommodating cavity; wherein the over torque protection mechanism comprises a thin column fixed on a bottom surface of the driving part; the loading part includes a groove with an upward opening, the groove and the bottom surface of the driving part form the closed accommodating cavity, and a baffle is disposed in the groove; the loading part is driven to rotate through cooperation of the thin column and the baffle; when a torque of the driving part acting on the over torque protection mechanism is larger than the threshold value, the thin column will be broken and/or the thin column will fall off from the bottom surface of the driving part.

2. The installation tool according to claim 1, wherein when the torque of the driving part acting on the over torque protection mechanism is larger than the threshold value, the over torque protection mechanism will be separated from the driving part and the loading part.

3. The installation tool according to claim 1, wherein a plurality of baffles are disposed in the groove, and the plurality of baffles divide the closed accommodating cavity into a plurality of chambers.

4. The installation tool according to claim 1, wherein a guide tube is disposed on a bottom surface of the driving part, the guide tube connects a lower end face of the loading part and an upper end face of the driving part, a boss located below the loading part is disposed on the outer wall of the guide tube, and a side wall of the guide tube is opened with an incision.

5. The installation tool according to claim 4, wherein the loading part further comprises an installation table, the installation table is disposed on a bottom surface of the loading part, and the installation table is set with a locking column.

* * * * *